United States Patent [19]

Elloy et al.

[11] Patent Number: 4,950,297
[45] Date of Patent: Aug. 21, 1990

[54] KNEE PROSTHESIS

[75] Inventors: Martin A. Elloy, North Yorkshire; Robert Johnson, Merseyside, both of England

[73] Assignee: Chas F Thackray Limited, West Yorkshire, England

[21] Appl. No.: 207,886

[22] Filed: Jun. 14, 1988

Related U.S. Application Data

[63] Continuation of Ser. No. 6/811,008, Dec. 19, 1985, abandoned.

[30] Foreign Application Priority Data

Dec. 20, 1984 [GB] United Kingdom ............... 8432267

[51] Int. Cl.5 .................................. A61F 2/38
[52] U.S. Cl. ........................................ 623/20
[58] Field of Search ........................ 623/18–20, 623/22, 23

[56] References Cited

U.S. PATENT DOCUMENTS

| | | | |
|---|---|---|---|
| 4,224,697 | 9/1980 | Murray et al. | 623/20 |
| 4,231,122 | 11/1980 | Koeneman | 623/20 |
| 4,257,129 | 3/1981 | Volz | 623/20 |
| 4,634,444 | 1/1987 | Noiles | 623/20 |

FOREIGN PATENT DOCUMENTS 2120943 12/1983 United Kingdom ............... 623/20

Primary Examiner—Alan W. Cannon
Attorney, Agent, or Firm—Darby & Darby

[57] ABSTRACT

A knee prosthesis comprises tibial, meniscal and femoral components. Subluxation and/or rotation of the meniscal component with respect to the tibial component is controlled by means of a control peg 21 fitted between the tibial and meniscal components, and a bar 5 spanning the intercondylar notch of the femoral component provides posterior stabilization by bearing against a cam surface 8 of a protrusion extending upwardly from the center of the meniscal component.

7 Claims, 4 Drawing Sheets

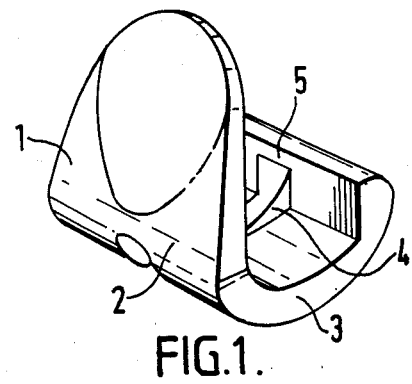
FIG.1.
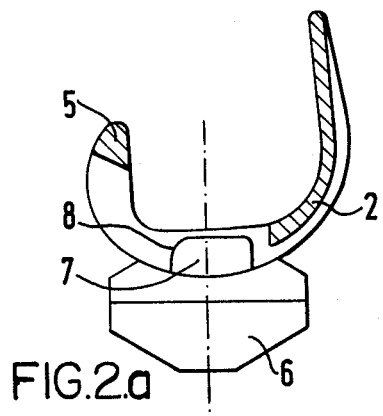
FIG.2.a
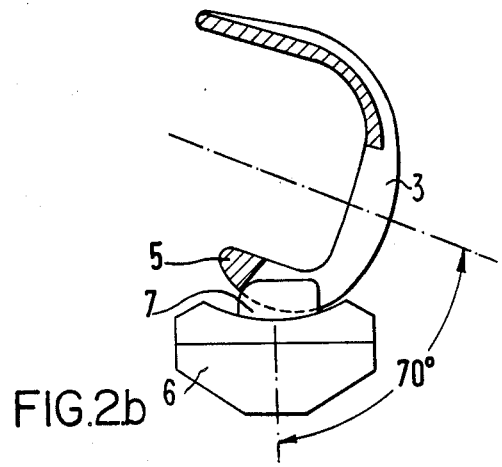
FIG.2.b
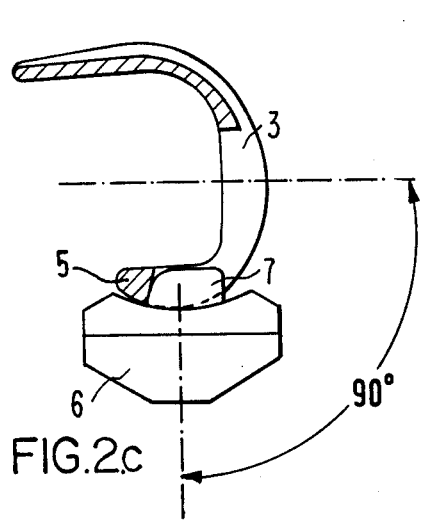
FIG.2.c
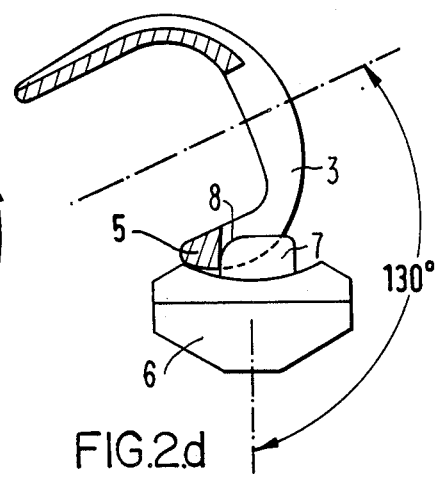
FIG.2.d

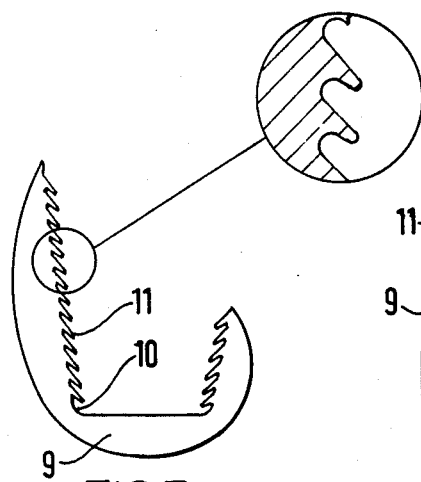
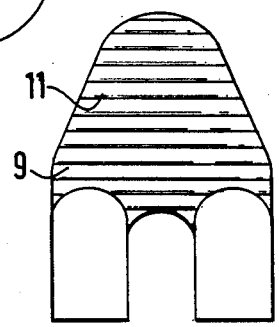
FIG.3.a  FIG.3.b
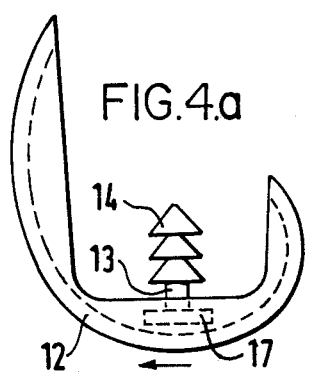
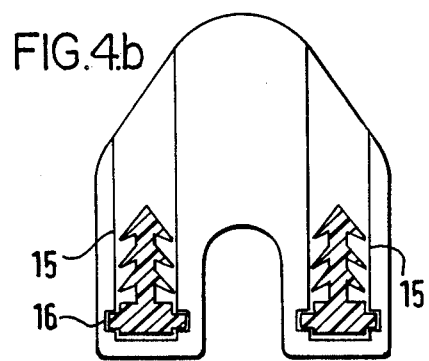
FIG.4.a  FIG.4.b
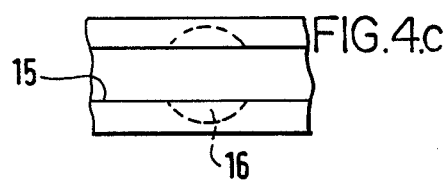
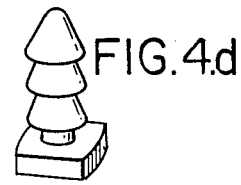
FIG.4.c  FIG.4.d
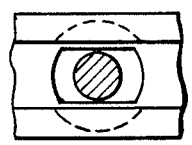
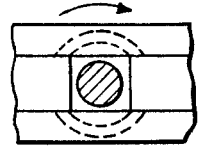
FIG.4.e  FIG.4.f

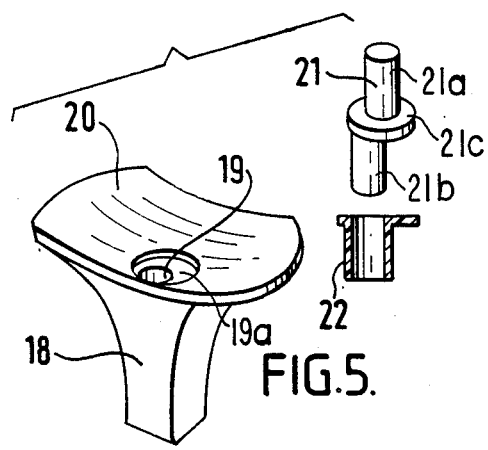
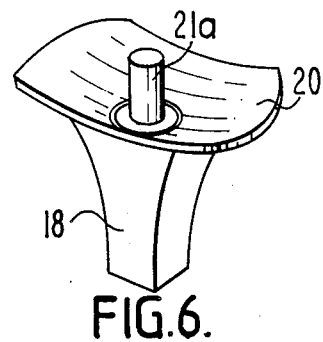
FIG.5.  FIG.6.
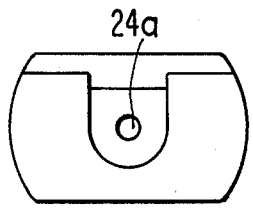
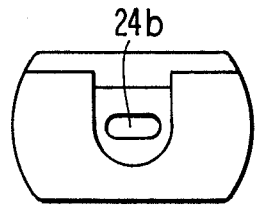
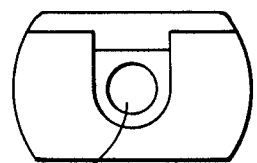
FIG.7a  FIG.7b  FIG.7c
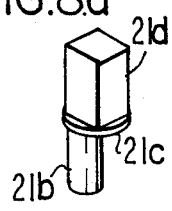
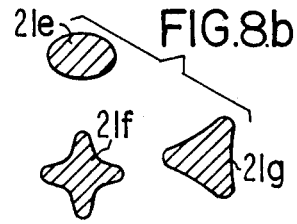
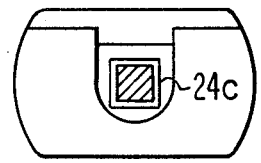
FIG.8a  FIG.8b  FIG.8c
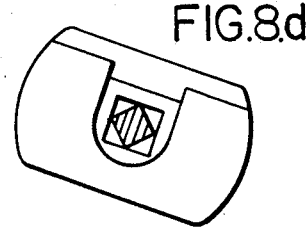
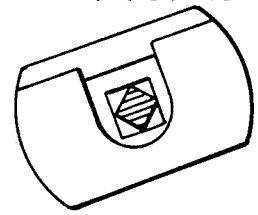
FIG.8d  FIG.8e

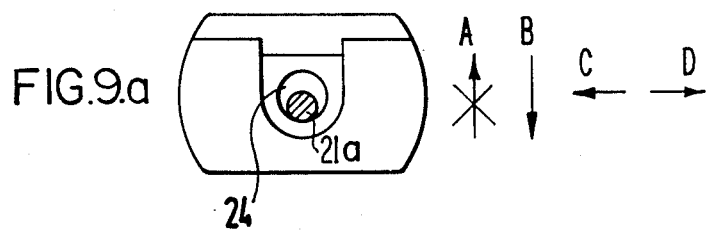
FIG.9.a
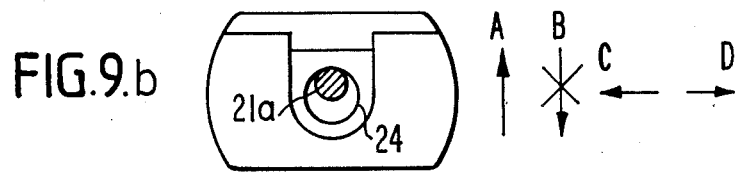
FIG.9.b
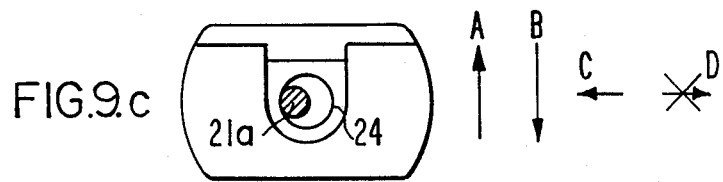
FIG.9.c
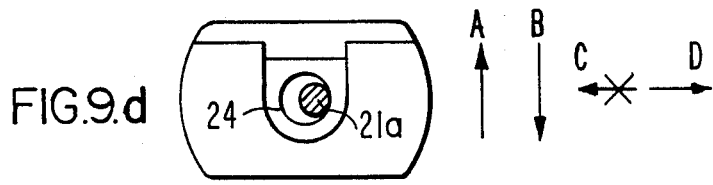
FIG.9.d

KNEE PROSTHESIS

This is a continuation of co-pending application Ser. No. 811,008 filed on Dec. 19, 1985 now abandoned.

This invention relates to endo-prosthetic knee joint devices.

Knee prostheses may be of the "constrained" type or of the "non-constrained" type. The former type replaces the functions of the bearing surfaces and of the ligaments and may take the form of a hinge. The latter type makes use of some or all of the natural ligaments to control the mode of articulation and/or prevent the separation of the opposing bearing surfaces of the prosthesis. This invention is concerned with knee prostheses of the non-constrained type.

A natural knee articulates both in flexion and rotation, the freedom to rotate increasing from zero at full extension to a maximum at full flexion. Flexion occurs about an axis which lies approximately perpendicular to tibia and parallel to the frontal plane. This axis is, however, not fixed but moves backwards as flexion increases. Rotation occurs about the long axis of the tibia. The locus of the flexion axis and the limit to rotational freedom is determined by the shapes of the opposing bearing surfaces (condyles) of femur and tibia and also the inextensible length and positions of insertion of four ligaments which connect the femur to the tibia. These ligaments comprise two collateral ligaments and two cruciate ligaments. Non-congruity of opposing condyles allows a complex articulation. Load distribution is achieved by two intervening semi-lunar cartilages or meniscii. These meniscii approximately conform to the femoral surfaces and are free to move relative to the tibial condyles.

A typical knee prosthesis includes a femoral component for attachment to the femur and tibial component for attachment to the tibia. Many knee prosthesis also include a meniscal component which is interposed between the femoral and tibial components. The femoral component and tibial component are usually attached to the bone using cement.

A first aspect of the present invention relates to a knee prosthesis which is in three parts. The prosthesis comprises a femoral component for attachment to the femur, a tibial component for attachment to the tibia and a meniscal component to lie between the fermoral and tibial components. The fermoral component has a bearing surface which is tangentially curved about medio-lateral axes and the meniscal component has a bearing surface complementary to the femoral bearing surface. The tibial component has a concave curved surface and the meniscal component has a bearing surface complementary to the tibial component's bearing surface.

The bearing surface of the fermoral component comprises two condylar tracks joined by a patella bearing surface.

Between the two condylar tracks is a gap which approximates to the intercondylar notch of the natural femur. The upper surface of the meniscal component has two co-axial cylindrical tracks complementary to the condylar bearing surface of the femoral component.

With a knee prosthesis such as that described in British Published Patent Specification No. 2120943 in which the bearing surfaces of the meniscal and tibial components are conical such that relative axial rotation is possible between the tibial and meniscal components and subluxation of the meniscal component is allowed, it would be advantageous to provide means for restricting subluxation of the meniscal component, particularly in cases where the natural knee ligaments are damaged or weakened.

A natural knee includes two pairs of ligaments which control movement of the knee. One pair, the cruciate ligaments, passes directly between the femur and the tibia in the central region of the joint, and thus in a joint replacement operation these crutiate ligaments may have to be removed. However, the other pair, known as the collateral ligaments, passes between the tibia and femur at the sides of the bones and can therefore be left in place.

It has been found that the collateral ligaments give the knee joint a lot of its stability and prevent the bones from coming apart. Thus if the ligaments are healthy and working as they should, it has been found that it is preferable to allow the meniscal component to subluxate to a great degree. This is because the collateral ligaments will prevent any dislocating forces from dislodging the meniscal component from the tibial component, as shown in British Published Patent Specification No. 2120943. However, if the collateral ligaments have been damaged or weakened and are not therefore constraining the knee properly, then a dislocating force on the knee could damage such a knee since the meniscal component would be free to completely "ride out" of the tibial component, or move to an unstable position.

According to the first aspect of the present invention there is provided a knee prosthesis comprising a femoral component for attachment to a femur and having a convex bearing surface which is tangentially curved about medio-lateral axes, a tibial component for attachment to a tibia and having a concave bearing surface, and a meniscal component to lie between the femoral and tibial components, said meniscal component having an inferior convex bearing surface complementary to that of the tibial component and a superior concave bearing surface complementary to that of the fermoral component, the inferior bearing surface of the meniscal component and the bearing surface of the tibial component both being conical such that relative axial rotation is possible between said tibial and meniscal components, the meniscal component including a recess in the base of its inferior bearing surface and a control peg being provided at the bearing surface of the tibial component, the control peg fitting in the recess in the meniscal component to control the subluxation thereof.

The control peg is preferably detachable from the tibial component, the tibial component having an alignment hole extending therethrough, the control peg fitting into said alignment hole in the tibial component.

The advantage of this particular preferred feature is that when the knee prosthesis is being fitted, an alignment rod may be inserted through the tibial component while the peg is removed and then after the tibial component is fitted, the alignment rod is removed and the peg may be replaced.

Such a tibial component has an alignment hole extending therethrough for the purpose of fitting the prosthesis as described above, and preferably a plastic sleeve is, at least in use, located between the control peg and the inside of the alignment hole to key the peg within the hole.

Because the axis of rotation of the knee prosthesis needs to be located behind the axis of the alignment hole in the tibial component, preferably the control peg comprises two portions, an inferior portion for inserting into the alignment hole and a superior portion for inserting within the recess in the inferior bearing surface of the meniscal component, the longitudinal axes of said inferior and superior portions being laterally offset from each other, and the two portions being rigidly connected together by means of a collar which, in use, fits into a correspondingly shaped recess in the bearing surface of the tibial component, the alignment hole lying eccentrically within the recess in the tibial component.

The control peg may control the relative movements of the tibial and meniscal components in a number of different ways.

The meniscal component may be exactly the same size as the control peg in the bearing surface of the tibial component so that subluxation is prevented and rotation only is allowed.

Alternatively, the recess in the inferior bearing surface of the meniscal component comprises a slot which allows subluxation in one direction only.

In still further alternative embodiments, the recess comprises a round hole of larger diameter than the control peg to allow limited subluxation in any direction, or alternatively the peg and recess are of non-round shape to provide a limited rotational freedom.

The use of a contral peg in this way to control subluxation means that posterior stabilisation may be utilised in the knee prosthesis.

Preferably, this is provided by producing a knee prosthesis in which the femoral component has a bearing surface comprising a patella-bearing area and a pair of condylar tracks which are tangentially curved about medio-lateral axes, a space being defined between the condylar tracks, and in which the meniscal component lying between the fermoral and tibial components has bearing surfaces complementary to said pair of condylar tracks of the femoral component and to the bearing surface of the tibial component, and in which a bar extends between the condylar tracks of the femoral component at the posterior portion of the tracks and a central projection is provided on the meniscal component such that the bar engages the rear of the centrally placed projection to cause the femoral component to roll to the back of the meniscal component.

This means that the range of flexion of the prosthesis is increased.

Preferably, the posterior surface of the meniscal component is cured to form a cam surface against which the bar moves.

More preferably, the prosthesis includes a bar which is of curved cross section.

The advantage of the bar formed on the femoral component is that it is not necessary to resect any additional bone from the intercondylar region of the femur to accommodate the femoral component. The normal resection required to fit the prosthesis is sufficient, and the intercondylar projection on the meniscal component simply fits into the space provided by the gap between the two condylar sections of the femoral component. The bar drives the meniscal component, and through this the tibial component, forward at high degrees of flexion so that the movement of the knee prosthesis simulates the function of the posterior cruciate ligament.

A second aspect of the present invention relates to means for fixing the fermoral component on the end of the femur without the use of bone cement.

In surgery, it is preferable to be able to use as little cement as possible since the introduction of cement between the prosthesis and the bone introduces a further interface which increases the risk of infection. Whilst it is becoming possible to avoid the use of cement in the fixation of tibial components to the tibia, since they tend to be inserted into the end of the tibia, and any forces on the component tends to force the component into the bone, the case is different with the femoral component which tends to be placed over the end of the femur. Also the knee exerts shearing and tipping forces on the femoral component with respect to the femur.

According to a second aspect of the present invention there is provided a femoral component for a knee prosthesis, said femoral component having an inner bone contacting surface and an outer bearing surface, in which the component includes on its inner bone contacting side a serrated surface which serves to key the femoral component to the bone without the use of cement, the angle of the serrations being such that the femoral component will push easily onto the femur but will resist any forces tending to pull the femoral component away from the femur.

The serrated surface may be integral with the femoral component. In this case, since the femoral component is often metallic, when the component is placed over the end of the resected femur, the bone is deformed, and then returns to its normal position which helps to prevent distraction of the component.

The elasticity of the bone causes recovery after passage of the serrations to engage the undercut of the trailing edge. The serrations are oriented such that they offer the least resistance to insertion and maximum resistance to distraction.

For long term fixation, tissue ingrowth into bone features on the implant surfaces required, usually combined with a wedging action to produce sufficient stability to maintain the prosthesis bone apposition during the healing process. The wedging action is produced by producing a femoral component and resecting the femur into complementary wedge shapes. This means that as the femoral component is pushed onto the femur it is tightened into position.

In an alternative embodiment, the serrated surface may be provided by at least one upwardly extending protrusion, said protrusion having a base member for locating within a correspondingly shaped slot in the femoral component, and an upper member extending from said base member and including a plurality of conical structures connected together in such a manner as to allow compression of said upper member when the femoral component is being pushed onto the femur, and extension of said upper member should any forces be applied tending to pull the femoral component away from the femur.

Examples of several knee prostheses in accordance with aspects of the invention will now be described, by way of example only, with reference to the accompanying drawings in which:

FIG. 1 is a perspective view of a femoral component in accordance with the first aspect of the invention;

FIGS. 2(a), 2(b), 2(c) and 2(d) are schematic views showing the flexion of the knee of FIG. 1;

FIGS. 3(a) and 3(b) are schematic views of a femoral component in accordance with the second aspect of the invention;

FIGS. 4(a) through 4(f) are schematic views of a second example of a femoral component in accordance with the second aspect of the invention;

FIG. 5 is an exploded perspective view of a tibial component in accordance with the first aspect of the invention;

FIG. 6 is a perspective view of the tibial component shown in FIG. 5;

FIGS. 7(A) through 7(C) are schematic views of examples of recesses in the meniscal component;

FIGS. 8(a), 8(b), 8(c), 8(d) and 8(e) represent a schematic view of further examples of pegs for fitting in the tibial component of FIG. 5; and, FIGS. 9(a) through 9(d) are schematic views showing the asymmetric stability provided by an eccentric post, or recess.

An example of knee prosthesis in accordance with the first aspect of the present invention includes a femoral component 1 as shown in FIGS. 1 and 2. The femoral component includes a bearing surface comprising a patella bearing area 2 and two condylar tracks 3. The condylar tracks are tangentially curved about mediolateral axes. A gap 4 is defined between the two tracks 3. At the posterior end of the condylar tracks 3 is a bar 5 which extends between the tracks.

The prosthesis also includes a meniscal component 6 including two condylar tracks complementary to the condylar bearing surfaces 3 of the femoral component between which is centrally disposed meniscal projection 7. The meniscal projection fits between the intercondylar space on the femoral component. The posterior corner of the projection 8 is curved. When the knee is in full extension the projection is centrally disposed in the femoral component. As the knee is flexed the femoral component 1 slides forward with respect to the meniscal component 6 until bar 5 engages the rear of projection 7.

The bar engaging the projection 7 prevents further forward sliding of the femoral component and therefore causes the femoral component to roll backwards on the meniscal component during further flexion. The resultant backwards displacement of the axis of flexion increases the range of flexion that can be achieved without tissue entrapment or bone impingement such that a flexion in the region of 150° may be achieved.

In an example of a knee prosthesis in accordance with the second aspect of the invention a femoral component 9 includes on its inner surface 10 serrations 11 which project inwardly. The serrations 11 are rigid, since they are integral with the femoral component 9 and are therefore made of metal. The elasticity of the bone allows it to deform, as the femoral component 9 is inserted over the resected femur, and subsequently relax so that distraction of the component 9 is prevented.

A second example of a femoral component 12 in accordance with the second aspect of the invention makes use of two members 13 each comprising a stack of conical flanges. The flanges 14 may be made of a flexible plastics material which deform under insertion but which help prevent removal of the component when the members 13 are in place. Each condylar track of femoral component 9 includes a groove 15 which includes a slot 16 cut from the side of the component. At the base of each member 13 is a flange which has a width such that it can be placed within the groove but a length which is wider than the groove. Thus the peg is slid into the groove and rotated until the flange 17 engages in the slot 16 to prevent the peg 13 being removed from the femoral component. The conical projections 14 help key the femoral component 12 into position on the femur.

Examples of prosthesis in accordance with the first aspect of the present invention are shown in FIGS. 5 to 9.

If a tibial component 18 is to be used in many different types of knee operation, a bore 19 is included at the base of its conical bearing surface 20. If the tibial component 18 is to be used in a joint where either of the collateral ligaments are damaged a peg 21 is fixed into place using plastic bush 22. The control peg 21 conveniently comprises an inferior portion 21b for inserting in the alignment hole 19 which is eccentrically bored in the tibial component, and a superior portion 21a for inserting within the recess 24 in the meniscal component. The two portions 21a, 21b are rigidly connected together by means of a collar 21c and are laterally offset from each other. When the inferior portion 21b is inserted in the alignment hole 19, the collar 21c fits into a corresponding recess 19a around the top of the alignment holes. As shown in FIG. 6, when inserted into the alignment hole 29a in the tibial component 18, all that can be seen of the control peg 21 is the superior portion 21a of the control peg protruding upwardly from the tibial plateau 20.

Referring now to FIGS. 7A, 7B and 7C, the recess 24 in the inferior surface of the meniscal component may take the form of a round hole 24a the same size as the superior portion 21a of the control peg which allows the meniscal plate to rotate but does not allow it to subluxate at all, or an elongate slot 24b which allows rotation and a limited subluxation in one direction only (along the length of the slot), or a round hole 24 of larger size than the superior portion 21a of the control peg, which allows rotation and limited subluxation in any direction.

FIG. 7 shows the different shaped recesses which may be used for different knee problems. In 7A the recess is the same size as the peg 21 so that no subluxation at all would be possible. This would be necessary if the ligaments were severely damaged.

If the recess is a slot or a larger diameter hole then the subluxation is allowed but is limited. This is for lesser degrees of damage to the ligaments.

In some cases it may be necessary to prevent or reduce relative rotation of the meniscal component and the tibial component. This is achieved by using non-round pegs 23. A square peg 21d fitting into a slightly larger square recess 24c will prevent rotation altogether, whereas other peg shapes such as oval (21e), star-shaped (21f) or triangular (21g) will reduce the tendency of the meniscal plate to rotate.

FIG. 9 illustrates how the direction of subluxation may be controlled by changing the position of the peg 22 with respect to a larger diameter hole 24.

FIGS. 9(a), 9(b), 9(c) and 9(d) illustrate how the peg and recess cooperate to control subluxation of the meniscal plate. In FIG. 9a, the plate has slid in the direction A until the peg 21a engages the edge of recess 24, at which point no further movement in direction A is allowed, only movement in directions B, C and D being allowed.

In FIG. 9(b), the plate has slid in direction B until the peg 21a engages edge of recess 24, at which point no further movement in direction B is allowed, only movements in directions A, C and D being allowed.

In FIG. 9(c), the plate has slid in direction D until the peg 21a engages the edge of recess 24, at this point no further movement is allowed in direction D, only movement in directions A, B and C being allowed.

In FIG. 9(d), the plate has slid in direction C until the peg 21a engages the edge of recess 24, at which point no further movement is allowed in direction C, only movements in directions A, B and D being allowed.

We claim:

1. An un-constrained knee prosthesis having a longitudinal axis extending in a direction corresponding to the general longitudinal direction of the long axis of the tibia, comprising in longitudinally successive relation along said axis:

an upper femoral component for attachment to a femur and having a pair of condylar tracks which are tangentially curved about medio-lateral axes and which are provided with posterior track portions having a bar extending therebetween;

a meniscal component disposed longitudinally below the femoral component and having an inferior convex frustoconical bearing surface and a superior concave bearing surface, the meniscal component engaging in longitudinally un-constrained manner with the condylar tracks of the femoral component via said superior concave bearing surface for un-constrained longitudinal relative movement therebetween along said axis;

a tibial component disposed longitudinally below the meniscal component for attachment to a tibia and having a concave frusto-conical bearing surface, the latter surface engaging in longitudinally unconstrained manner with the inferior bearing surface of the meniscal component for unconstrained longitudinal relative movement therebetween along said axis;

a selectively sized and shaped control peg extending upwardly from said bearing surface of the tibial component and being detachable from the tibial component;

a recess formed in the inferior bearing surface of the meniscal component to receive the control peg remote from the femoral component and in a manner which selectively controls subluxation of the meniscal component; and a central projection provided in the superior bearing surface of the meniscal component and operable independently of the control peg to engage said bar during flexion of the knee in order firstly to limit relative sliding between the condylar tracks of the femoral component and the superior bearing surface of the meniscal component and thereafter to allow a backwards rolling motion of said tracks on the meniscal component as the knee approaches full flexion.

2. A prosthesis according to claim 1 in which said central projection is provided with a posterior portion and said posterior portion is curved.

3. A prosthesis according to claim 1 in which said bar is of curved cross section.

4. A prosthesis according to claim 1 in which said recess comprises a round hole of larger diameter than the control peg to allow limited subluxation in any direction.

5. A prosthesis according to claim 1 in which the tibial component has an alignment hole and the control peg fits into said alignment hole in the tibial component.

6. A prosthesis according to claim 5 in which a plastic sleeve is, at least in use, located between the control peg and the inside of said alignment hole to key the peg within said hole.

7. An un-constrained knee prosthesis having a longitudinal axis extending in a direction corresponding to the general longitudinal direction of the long axis of the tibia, comprising in longitudinally successive relation along said axis:

an upper femoral component for attachment to a femur and having a pair of condylar tracks which are tangentially curved about medio-lateral axes and which are provided with posterior track portions having a bar extending therebetween;

a meniscal component disposed longitudinally below the femoral component and having an inferior convex frustoconical bearing surface and a superior concave bearing surface, the meniscal component engaging in longitudinally un-constrained manner with the condylar tracks of the femoral component via said superior concave bearing surface for un-constrained longitudinal relative movement therebetween along said axis;

a tibial component disposed longitudinally below the meniscal component for attachment to a tibia and having a concave frusto-conical bearing surface, the latter surface engaging in longitudinally unconstrained manner with the inferior bearing surface of the meniscal component for unconstrained longitudinal relative movement therebetween along said axis;

a control peg extending upwardly from said bearing surface of the tibial component and being detachable from the tibial component, the tibial component having an alignment hole and the control peg fitting into the alignment hole;

a recess formed in the inferior bearing surface of the meniscal component to receive the control peg in a manner which controls subluxation of the meniscal component;

the control peg comprising two peg portions, an inferior portion for inserting into the alignment hole and a superior portion for inserting within the recess in the inferior bearing surface of the meniscal component, said inferior and superior portions having longitudinal peg axes which are laterally offset from each other, and the two peg portions being rigidly connected together by means of a collar which, in use, fits into a correspondingly shaped recess in said bearing surface of the tibial component, the alignment hole lying eccentrically within said correspondingly shaped recess in the tibial component; and a central projection provided in the superior bearing surface of the meniscal component and operable independently of the control peg to engage said bar during flexion of the knee in order firstly to limit relative sliding between the condylar tracks of the femoral component and the superior bearing surface of the meniscal component and thereafter to allow a backwards rolling motion of said tracks on the meniscal component as the knee approaches full flexion.

* * * * *